United States Patent [19]
Drent

[11] Patent Number: 4,940,787
[45] Date of Patent: Jul. 10, 1990

[54] PROCESS FOR THE CARBONYLATION OF ACETYLENIC UNSATURATED COMPOUNDS

[75] Inventor: Eit Drent, Amsterdam, Netherlands

[73] Assignee: Shell Oil Company, Houston, Tex.

[21] Appl. No.: 125,263

[22] Filed: Nov. 25, 1987

[30] Foreign Application Priority Data

Dec. 5, 1986 [NL] Netherlands ............... 8603100

[51] Int. Cl.⁵ ............. C07H 1/00; C07C 51/10; C07C 51/14
[52] U.S. Cl. ................. 536/124; 536/1.1; 536/119; 562/406; 562/522; 562/890; 556/136; 260/410.6; 560/207; 560/104
[58] Field of Search ........... 536/1.1, 124; 562/406, 562/522; 260/410.6, 546, 548; 556/136

[56] References Cited

U.S. PATENT DOCUMENTS 3,887,595 6/1975 Nazaki ............... 260/410.6
4,257,973 3/1981 Mrowca ............ 260/410.9 R
4,739,110 4/1988 Drent ................. 562/406

FOREIGN PATENT DOCUMENTS 186228 2/1986 European Pat. Off. .

Primary Examiner—Ronald W. Griffin
Assistant Examiner—Everett White
Attorney, Agent, or Firm—Y. Grace Tsang

[57] ABSTRACT

A method for the preparation of alpha,beta-olefinic unsaturated compounds by means of carbonylation of acetylenic unsaturated compounds with carbon monoxide in the presence of a hydroxy-containing compound in liquid phase, accomplished in the presence of a catalytic system that can be formed from:

(a) a palladium compound,
(b) a protonic acid, and
(c) an organic phosphine according to the formula:

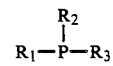

wherein $R_1$ represents a heterocyclic five- or six-atom ring, comprising, at least as hetero atom, nitrogen, which may be optionally substituted and/or may form part of a larger condensed ring structure that may be optionally substituted, and wherein $R_2$ and $R_3$ each have the aforesaid meaning of $R_1$ or may represent an optionally substituted aryl group.

The invention further comprises novel organic phosphines and compositions containing said phosphines as wel as the catalytic systems containing said phosphines.

33 Claims, No Drawings

PROCESS FOR THE CARBONYLATION OF ACETYLENIC UNSATURATED COMPOUNDS

FIELD OF THE INVENTION

The invention relates to a process for the carbonylation of an acetylenic unsaturated compound with carbon monoxide in the presence of a palladium- and organic phosphine-containing catalytic system. The invention also includes a novel organic phosphine and a novel catalyst containing a palladium compound and said organic phosphine.

BACKGROUND OF THE INVENTION

It is known that acetylenic unsaturated compounds can be carbonylated in the presence of a hydroxyl-containing compound such as an alcohol, phenol water or a carboxylic acid to produce alpha,beta-olefinic unsaturated esters, acids or anhydrides, respectively.

In all cases, the known methods exhibit low selectivity towards the desired compounds and a relatively low conversion rate whereby they are regarded as unattractive for use on a commercial scale.

As a result of that opinion on the part of those skilled in the art, as, for example, transpires from column 2, lines 53–56, of U.S. Pat. specification No. 3,887,595, issued June 3, 1975, those skilled in the art have not been primarily inclined to direct further research towards that type of reaction in the search for methods for the preparation of cheaper and attractive base materials desired for further organic syntheses. On the other hand, the demand for cheaper base materials desired for further organic chemical syntheses has been steadily growing over the years.

The purpose of the invention is therefore to provide an improved method for the preparation of alpha,beta-olefinic unsaturated esters, acids or anhydrides.

SUMMARY OF THE INVENTION

As a result of extensive research and development, an improved method has now been found for the preparation of alpha,beta-olefinic unsaturated compounds by means of the carbonylation of an acetylenic unsaturated compound with carbon monoxide in the presence of a hydroxyl-containing compound in liquid phase, accomplished in the presence of a catalytic system formed from:
(a) a palladium compound,
(b) a protonic acid, and
(c) an organic phosphine according to the formula:

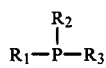
(I)

wherein $R_1$ is selected from the group consisting of a nitrogen-containing heterocyclic five-atom ring, a nitrogen-containing heterocyclic six-atom ring, a fused ring comprising at least one nitrogen-containing five-atom ring and a fused ring comprising at least one nitrogen-containing six-atom ring; wherein $R_2$ and $R_3$ are each $R_1$ or an aryl group.

The present invention further includes a novel palladium containing catalytic system formed from the aforementioned formula (a), (b), and (c).

The present invention still further includes a novel organic phosphine according to Formula I specified in (c).

DETAILED DESCRIPTION OF THE INVENTION

The organic phosphine which is the key part of the invention has the following general formulation I:

wherein $R_1$ is selected from the group consisting of a nitrogen-containing heterocyclic five-atom ring, a nitrogen-containing heterocyclic six-atom ring, a fused ring comprising at least one nitrogen-containing five-atom ring and a fused ring comprising at least one nitrogen-containing six-atom ring; wherein $R_2$ and $R_3$ are each $R_1$ or an aryl group.

As used herein, the terms heterocyclic ring, fused ring and aryl group shall include substituted as well as unsubstituted rings (groups).

When the phosphine is used for the catalysis of the carbonylation reaction of the present invention, the substituent must be one which would not adversely affect said carbonylation reaction.

Examples of heterocyclic rings according to the definitions of $R_1$, $R_2$, and $R_3$ are pyridyl, pyrazinyl, quinolyl, isoquinolyl, pyrimidinyl, pyridazinyl, indolizinyl, cinnolinyl, acridinyl, phenazinyl, phenathridinyl, phenanihrolinyl, phthalazinyl, naphthyridinyl, quinoxalinyl and quinazolinyl. Of those groups, pyridyl, pyrazinyl and pyridazinyl are preferred.

Said heterocyclic groups and the aforesaid aryl groups according to the definitions of $R_1$, $R_2$, and $R_3$ may be substituted with one or more electron-repelling or electron-attracting groups. Examples of electron-repelling substituents on the aforesaid groups are alkoxy groups, particularly the ortho and para-substituted alkoxy group substituents, and in particular those with not more than 5 carbon atoms, for example, melhoxy and elhoxy groups, alkyl groups with not more than 5 carbon atoms, such as methyl, ethyl, n-propyl, isopropyl-tert-butyl or dimethylamino and diethylamino groups.

Examples of electron-attracting substituents on the aforesaid groups are halogenic such as chlorine and fluorine, irifluoromethyl, trichloromethyl, monochloromethyl and m-methoxy groups.

The substituted or unsubstituted aryl groups of the definitions $R_2$ and $R_3$ contain not more than 18 carbon atoms in the ring system and may consist of anthryl, naphthyl and, preferably, phenyl.

Phosphines according to the general Formula I wherein $R_1$ represents a pyridyl and $R_2$ and $R_3$ represent a substituted or an unsubstituted phenyl are preferred.

In a preferred embodiment of the invention, when diphenyl-2-pyridylphospine is used, it not only fives very high selctivities towards alpha, beta-olefinic unsaturated acids or esters, but also produces very high yields. Other examples of suitable phosphines are:
di(p-methoxyphenyl) 2-pyridylphosphine
di(p-tolyl) 2-pyridylphosphine
di(p-tolyl) 2-pyridylphosphine
di(o-methoxyphenyl) 2-pyridylphosphine
di(o-chlorophenyl) 2-pyridylphosphine
di(methoxyphenyl) 2-pyridylphosphine
di(m-chlorophenyl) 2-pyridylphosphine di(p-methoxyphenyl) 3-pyridylphosphine
di(p-tolyl) 3-pyridylphosphine
di(o-methoxylphenyl) 3-pyridylphosphine
di(o-chlorophenyl) 3-pyridylphosphine
di(m-methoxyphenyl) 3-pyridylphosphine
di(m-chlorophenyl) 3-pyridylphosphine
di(p-methoxyphenyl) 4-pyridylphosphine
di(p-tolyl) 4-pyridylphosphine
di(o-methoxyphenyl) 4-pyridylphosphine
di(o-chlorophenyl) 4-pyridylphosphine
di(m-methoxyphenyl) 4-pyridylphosphine
di(m-chlorophenyl) 4-pyridylphosphine
diphenyl(3-methoxy-2-pyridyl) phosphine
diphenyl(4-methoxy-2-pyridyl) phosphine
diphenyl(4-chloro-2-pyridyl) phosphine
diphenyl(2-methoxy-3-pyridyl) phosphine
diphenyl(4-methoxy-3-pyridyl) phosphine
diphenyl(4-chloro-3-pyridyl) phosphine
diphenyl(3-methoxy-4-pyridyl) phosphine
diphenyl(3-chloro-4-pyridyl) phosphine
diphenyl(5-chloro-4-pyridyl) phosphine
diphenyl(5-methoxy-4-pyridyl) phosphine
di(p-tolyl)(3-methoxy-4-pyridyl) phosphine
di(p-tolyl)(3-chloro-4-pyridyl) phosphine
di(m-methoxyphenyl)(3-chloro-4-pyridyl) phosphine
di(m-methoxyphenyl)(3-methoxy-4-pyridyl) phosphine
di(m-chlorophenyl)(3-methoxy-4-pyridyl) phosphine
di(p-tolyl)(3-methoxy-2-pyridyl) phosphine
di(p-tolyl)(3-chloro-2-pyridyl) phosphine
di(m-methoxyphenyl)(3-chloro-pyridyl) phosphine
di(m-methoxyphenyl)(3-methoxy-2-pyridyl) phosphine
di(m-tert.butoxyphenyl)(3-chloro-2-pyridyl) phosphine
di(m-tert.butoxyphenyl)(3-methoxy-2-pyridyl) phosphine
di(m-tert.butyoxyphenyl)(3-chloro-4-pyridyl) phosphine
di(m-tert.butoxyphenyl)(3-methoxy-4-pyridyl) phosphine
di(m-tert.butoxyphenyl)(2-methoxy-3-pyridyl) phosphine
di(m-tert.butoxyphenyl)(2-chloro-3-pyridyl) phosphine
di(m-chlorophenyl)(2-methoxy-3-pyridyl) phosphine
di(m-chlorophenyl)(2-chloro-3-pyridyl) phosphine
di(o-chlorophenyl)(2-methoxy-3-pyridyl) phosphine
di(p-methoxyphenyl) 2-pyrimidinylphosphine
di(p-tolyl) 2-pyrimidinylphosphine
di(o-methoxylphenyl) 2-pyrimidinylphosphine
di(o-chlorophenyl) 2-pyrimidinylphosphine
di(m-methoxylphenyl) 2-pyrimidinylphosphine
di(p-methoxylphenyl) 2-pyridazinylphosphine
di(p-tolyl) 2-pyridazinylphosphine
di(o-methoxylphenyl) 2-pyridazinylphosphine
di(o-chlorophenyl) 2-pyridazinylphosphine
di(m-methoxyphenyl) 2-pyridazinylphosphine
di(p-methoxyphenyl)(3-methoxy-2-pyrimidinyl) phosphine
di(p-tolyl)(3-methoxy-2-pyridinyl) phosphine
di(o-chlorophenyl)(3-chloro-2-pyrimidinyl) phosphine
di(m-methoxyphenyl)(3-chloro-2-pyrimidinyl) phosphine
di(p-tolyl)(4-methoxy-3-pyridazinyl) phosphine
di(p-methoxyphenyl)(4-methoxy-3-pyridazinyl) phosphine
di(o-chlorophenyl)(4-methoxy-3-pyridazinyl) phosphine
phenyl di(3-methoxy-2-pyridyl) phosphine
phenyl di(4-methoxy-2-pyridyl) phosphine
phenyl di(4-chloro-2-pyridyl) phosphine
phenyl di(2-methoxy-3-pyridyl) phosphine
phenyl di(4-methoxy-3-pyridyl) phosphine
phenyl di(4-chloro-3-pyridyl) phosphine
phenyl di(3-methoxy-4-pyridyl) phosphine
phenyl di(3-chloro-4-pyridyl) phosphine
phenyl di(5-chloro-4-pyridyl) phosphine
phenyl di(5-methoxy-4-pyridyl) phosphine
phenyl di(3-methoxy-2-pyrimidinyl) phosphine
phenyl di(3-chloro-2-pyrimidinyl) phosphine
phenyl di(4-methoxy-2-pyrimidinyl) phosphine
phenyl di(4-methoxy-3-pyridazinyl) phosphine and
phenyl di(4-chloro-3-pyridazinyl) phosphine.

As protonic acid, a wide variety of acids or mixtures thereof may be used. Examples of such acids are: orthophosphoric acid, pyrophosphoric acid, sulfuric acid, hydrohalogenic acids, benzenephosphoric acid, benzenesulfonic acid, p-toluenesulfonic acid, naphthalenesulfonic acid, toluenephosphoric acid, chlorosulfonic acid, fluorosulfonic acid, monochloroacetic acid, dichloroacetic acid, trichloroacetic acid, trifluoroacetic acid, oxalic acid, terephthalic acid, perchloric acid, 2-hydroxypropane-2-sulfonic acid, trifluoromethanesulfonic acid or mixtures thereof, of said acids, paratoluenesulfonic acid and benzenephosphonic acid are preferred.

Hydrohalogenic acids can, in principle, be used but have the known drawback that they induce a corrosive effect.

Both homogeneous and heterogeneous palladium compounds may be used for the process according to the invention. Homogeneous compounds are preferred. Suitable homogeneous compounds are palladium salts of nitric acid, sulfuric acid or alkanecarboxylic acids with not more than 12 carbon atoms per molecule.

Salts of hydrohalogenic acids may, in principle, be used as well but these have the drawback that the halide ion may induce a corrosive effect.

Preferably, palladium acetate is used as catalyst component. Palladium complexes may also be used such as palladium acetylacetonate, tetrakis-triphenylphosphinepalladium, bis-tri-o-tolyl-phosphinepalladium acetate or bis-diphenyl-2-pyridylphosphinepalladium acetate, tetrakis-diphenyl-2-pyridylphosphinepalladium and bis-di-o-tolylpyridylphosphinepalladium acetate or bis-diphenyl-pyridylphosphinepalladium sulfate.

The quantity of the palladium compound is not critical. Preferably, quantities are used within the range of $10^{-7}$ to $10^{-1}$ gram atom palladium per mole acetylenic unsaturated compound.

The molar ratio of the organic phosphine to palladium is not critical and may vary between wide limits.

Very high selectivity, i.e., greater than 98%, and high conversion rates, for example, 10,000–40,000 mole/g atom Pd/hour are achieved if more than 2 and preferably less than 500 mole organic phosphine are used per gram atom palladium. In general, quantities of more than 1,000 mole organic phosphine per gram atom palladium are not necessary.

The number of protonic acid equivalents used per organic phosphine equivlalent is not critical and may vary between wide limits. Quantities in the range of 0.1 to 50 protonic acid equivalents per organic phosphine equivalent are preferably used.

A separate solvent is not essential for the process according to the invention.

A large excess of one of the reactants, mostly the alcohol, can often form a suitable liquid phase. In some cases, however, it may be desirable to use a separate solvent. Any inert solvent can be used for that purpose. Said solvent may, for example, be selected from sulfoxides and sulfones, for example, dimethylsulfoxide, diisopropylsulfone or tetrahydrothiophene-2,2-dioxide (also referred to as suliolane), 2-methylsulfolane, 3-methylsulfolane, 2-methyl-4-butylsulfolane; aromatic hydrocarbons such as benzene, toluene, xylenes; esters such as methylacetate and butyrolactone; ketones such as acetone or methyl isobutyl ketone and ethers such as anisole, 2,5,8-trioxanone (also referred to as diglyme) diphenyl ether and diisopropyl ether.

Particularly good results are achieved if N-methylpyrrolidone is used as a main solvent or as a co-solvent. It will be clear to those skilled in the art that the good effect of N-methylpyrrolidone (NMP) must be regarded as highly surprising on account of the known retarding effect of NMP on other alkene conversions of this type.

The method according to the invention allows the use of very mild reaction conditions. Temperatures in the range of 20° C. to 200° C. and in particular from 20° C. to 30° C. are suitable.

Pressure can vary over a wide range but will generally be lower than that employed in the hitherto known processes. Pressures from 5 to 70 bar are preferred. Pressures higher than 100 bar may be used, but are generally economically unattractive on account of special apparatus requirements.

The molar ratio of the hydroxyl alcohol containing compounds, e.g., alcohol, phenol, water or carboxylic acid, to the acetylenic unsaturated compounds may vary between wide limits and generally lies within the range of 0.01:1 to 100:1.

The process according to the invention can be accomplished with the use of a wide variety of acetylenic unsaturated compounds which under certain circumstances may carry one or more substituents that are inert under the reaction conditions in question, such as halogen atoms and cyano, ester, alkoxy and aryl groups. Moreover, the acetylenic unsaturated compounds may comprise one or more substituents that are not inert under the reaction conditions, for example, hydroxy groups. The behavior of such groups will depend on the precise reaction conditions. One or more acetylenic unsaturated bonds may be present in any position in the carbon chain.

Very good results have been achieved with unsubstituted alkynes and in particular with those with up to 20 carbon atoms per molecule, and more particularly with acetylene, propylene and phenylacetylene. Other examples of suitable alkynes are: 1-butyne, 2-butyne, 1-pentyne, 1-hexyne, 1-heptyne, 1-octyne, 2-octyne, 4-octyne, 5-methyl-3-heptyne, 4-propyl-2-pentyne, 1-nonyne, benzylethyne and cyclohexylethyne. Alkynes can be used in pure form or in mixtures with alkenes. It has been found that the alkenes are inert under the reaction conditions.

An extensive series of hydroxyl compounds can be used as reagents in the process according to the invention. For example, the alcohol used may be aliphatic, cycloaliphatic or aromatic and may carry one or more inert substituents. A suitable alcohol may comprise up to 20 carbon atoms per molecule. One or more hydroxyl groups may be present, in which case several products may be formed, depending on the molar ratio of the reagents used. For example a polyvalent alcohol, in particular lower sugars such as glucose. fructose, mannose, galactose, sucrose, aldoxose, aldopentose, altrose, allose, talose, gulose, idose, ribose, arabinose, xylose, lyxose, erythrose and threose can be allowed to react with a small quantity of an acetylenic unsaturated compound in order to form a monoester, or with a large quantity of an acetylenic unsaturated compound in order to form a polyvalent ester. The choice of alcohol will therefore depend solely on the product desired. The use of water produces, in the first instance, alpha, beta-unsaturated carboxylic acids. The use of alchohols produces alpha, beta-unsaturated esters and these can naturally be the polyesters described hereinbefore. Alkanols such as methanol, ethanol, propanol or 2,2-dihydroxymethyl-1-butanol, and alcohols comprising ether bridges, such as, for example, triethylene glycol, all yield valuable products. Phenols are also quite suitable.

According to a preferred embodiment of the process according to the invention, lower sugars can be selectively converted to form monomers that can be further converted into attractive water-soluble polymers. Selectivity towards the product desired can be achieved by temporarily protecting hydroxyl groups that must not take part in the reaction, whereby exclusively primary or secondary hydroxyl groups can be allowed to react.

The process according to the invention can be accomplished with the use of a wide variety of carboxylic acids. For example, the carboxylic acids may be aliphatic, cycloaliphatic or aromatic and may carry one or more inert substituents, such as those named in connection with the acetylenic unsaturated compounds. Carboxylic acids suitable for use contain up to 20 carbon atoms. One or more carboxylic acid groups may be present whereby various products can be obtained as desired, depending on the molar ratio of the reactants used. The carboxylic acids may, for example, be alkanecarboxylic acids or alkenecarboxylic acids. Examples of suitable carboxylic acids are: formic acid, acetic acid, propionic acid, n-butyric acid, isobutyric acid, pivalic acid, n-valeric acid, n-caproic acid, acid, lauric acid, myristic acid, palmitic acid, stearic acid, benzoic acid, o-phthalic acid, m-phthalic acid, terephthalic acid and toluic acid. Examples of alkenecarboxylic acids are acrylic acid, propiolic acid, methacrylic acid, crotonic acid, isocrotonic acid, oleic acid, maleic acid, fumaric acid, citraconic acid and mesaconic acid.

If an alkenecarboxylic acid with n+1 carbons atoms per molecule reacts with an alkyne with n carbon atoms per molecule, a symmetrical anhydride is produced. In other cases, a composite anhydride is produced in the first instance, possibly followed by transesterization. If, for example, an excess of acetic acid is allowed to react according to the invention with propyne and carbon monoxide, a mixture of acetic anhydride and methacrylic acid will finally be formed.

If it is desired to produce a special acid by means of the method according to the invention, it may, for example be favorable to allow one mole of the acid in question to react with the corresponding alkyne having one carbon atom fewer in order to form the symmetrical anhydride, to hydrolyze the anhydride in order to form two moles of the acid and to recycle one mole of that acid to the first state of the process. Depending on the presence of further compounds, further reactions may take place, For example, if the process according to the invention is accomplished in the presence of an amine, that amine may react with the carboxylic anhydride to form a carboxylic acid and an amine cazboxylate. For example, the reaction of propyne with carbon monoxide and methacrylic acid in the presence of piperidine forms a high yield of 1-methacryloylpiperidine.

The carbon monoxide required for the process may be used in a practically pure form or diluted with some inert gas, for example, nitrogen. The presence of more than small quantities of hydrogen in the gas stream is undesirable on account of the hydrogenation of the acetylenic unsaturated compound that will then occur under the reaction conditions. In general, it is preferable for the quantity of hydrogen in the gas stream supplied to amount to less than 5 percent by volume.

The selectivity toward alpha,beta-olefinic unsaturated compounds, expressed as a percentage, is defined as $$\frac{a}{b} \times 100$$

wherein "a" is the quantity of acetylenic unsaturated compound converted into alpha,beta-olefinic unsaturated compound and "b" is the total quantity of acetylenic unsaturated compound that has been converted.

Another aspect of the present invention is formed by the organic phosphines according to the general Formula I, wherein $R_1$, $R_2$ and $R_3$ have in the meanings defined hereinbefore, as such or mixed with suitable quantities of a palladium compound and/or protonic acid, as defined hereinbefore, optionally dissolved or suspended in a separate solvent, preferably selected from dimethyl sulfoxide, diisopropyl sulfone, sulfolane, benzene, toluene, xylenes, methyl acetate, butyrolactone, acetone, methyl isobutyl ketone, anisole, diglyme, diphenyl ether and diisopropyl ether, and N-methylpyrrolidone.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention as defined by the instant specification and claims.

The invention is further expounded with the aid of the following Examples without, however, limiting its scope to them.

EXAMPLE 1

A 300 ml magnetically stirred HASTELLOY® autoclave was successively filled with 0.025 mmole palladium (II) acetate, 1 mmole diphenyl-2-pyridylphosphine, 2 mmole para-toluene sulionic acid and 50 ml methanol. Air was evacuated from the autoclave, whereupon propyne was added to a pressure of 2 bar. Subsequently, carbon monoxide was added to a pressure of 60 bar. The autoclave was sealed and heated to a temperature of 45° C. After a reaction time of two hours at 45° C. a specimen of the contents was analyzed by means of gas liquid chromatography. The selectivity of the conversion of propyne to methyl methacrylate was found to be 99% while the mean conversion rate was calculated to be 20,000 mole propyne/g.at.Pd/hour.

EXAMPLE 2

The experiment as described in Example 1 was repeated in a virtually analogous manner with the same reactants and catalyst system except that 10 ml propylene was also added, while the reaction was performed at 55° C. By means of gas liquid chromatographical analysis, it was found that propyne had been converted to methyl methacrylate with a selectivity of 99%, while the product obtained was found to comprise less than 0.2% butyrate as by-product, which indicates that there was hardly any conversion of the admixed propylene under the reaction conditions selected according to the invention. Mean reaction rate was calculated to be 20,000 mole propyne/g.at.Pd/hour.

EXAMPLE 3

The experiment as described in Example 1 was repeated in a virtually analogous manner except that 30 ml N-methylpyrrolidone was added as an extra solvent simultaneously with the methanol, while the reaction was performed at 40° C. with a reaction time of one hour. The selectivity of the propyne to methyl methacrylate conversion amounted to 99% while the mean conversion rate was calculated to be 40,000 mole propyne/g.at.Pd/hour.

EXAMPLE 4

The experiment as described in Example 1 was repeated in a virtually analogous mannez with a catalyst system composed of 0.025 mmole palladium (II) acetate, 1 mmole phenyl di(2-pyridyl)phosphine and 2 mmole para-toluene sulfonic acid, a reaction temperature of 75° C. and a reaction time of two hours. The selectivity of the propyne to methyl methacrylate conversion amounted to 98%, while the mean conversion rate was calculated to be 10,000 mole propyne/g.at.Pd/hour.

EXAMPLE 5

The example as described in Example 1 was repeated in a virtually analogous manner with a catalyst system composed of 0.025 mmole palladium (II) acetate, 1 mmol tri(pyridyl)phosphine and 2 mmol para-toluene sulfonic acid, a reaction temperature of 80° C. and a reaction time of five hours. The selectivity of propyne conversion amounted to 97% and the mean conversion rate was 1500 mole propyne/g.at.Pd/hour.

EXAMPLE 6

The experiment as described in Example 1 was performed in a virtually analogous manner with a catalyst system composed of 0.025 mmole palladium (II) acetate, 1 mmole diphenyl-(2-pyridyl)phosphine and 2 mmole benzenephosphonic acid. The reaction temperature was 50° C. and the reaction time five hours. Propyne was converted into methyl methacrylate with a selectivity of 99%, while the mean conversion rate amounted to 4000 mole propyne/g.at.Pd/hour.

EXAMPLE 7

An experiment as described in Example 1 was performed in a virtually analogous manner with a catalyst system composed of 0.2 mmole palladium (II) acetate, 2 mmole diphenyl-2-pyridylphosphine and 2 mmole benzenephosphonic acid, except that as reactant 10 ml methacrylic acid and 50 ml anisole as solvent were added prior to evacuation of the reactor. Reaction temperature was 115° C. and reaction time one hour. Propyne was converted to methacrylic anhydride with a selectivity of 98% while the mean conversion rate amounted to 1500 mole propyne/g.at.Pd/hour.

EXAMPLE 8

The experiment of Example 7 was repeated with 3 mmole diphenyl-2-pyridylphosphine, 10 g phenol and 50 ml anisole. Reaction temperature was 90° C. and reaction time one hour. Propyne was converted into phenyl methacrylate with a selectivity of 98%, while the mean conversion rate was 2000 mole propyne/g.at.Pd/hour.

EXAMPLE 9

In a virtually analogous manner as described in Example 1, an experiment was performed with a catalyst system composed of 0.025 mmole palladium (II) acetate, 1 mmole diphenyl-2-pyridyl-phosphine and 2 mmole para-toluene sulfonic acid, acetylene instead of propyne with an acetylene pressure of 1.4 bar, 30 ml methanol and as extra solvent (30 ml) N-methylpyrrolidone. The Reaction temperature was 40° C. and the reaction time one hour. The selectivity cf conversion of acetylene into methylacrylate was about 100%, while the calculated conversion rate was 2500 mole acetylene/g.at.Pd/hour.

EXAMPLE 10

In a virtually analogous manner as in Example 1, the reaction was performed with the same catalyst system as in Example 9, 20 ml phenylethyne, 30 ml methanol and 30 ml N-methylpyrrolidone. The reaction temperature was 40° C. and the reaction time one hour. Phenylethyne was converted into methyl phenylacrylate with a selectivity of 98% while the mean conversion rate was found to be 5500 mole phenylethyne/g.at.Pd/hour.

EXAMPLE 11

A virtually analogous experiment as in Example 10 was performed, except that now a catalyst system composed of 0.025 mmol palladium (II) acetate, 1 mmole phenyl di(2-pyridyl)phosphine and 2 mmole para-toluene sulfonic acid was used. The reaction temperature was 60° C. and the reaction time two hours. The selectivity of conversion of phenylethyne into methyl phenylacrylate was 98% and the mean conversion rate was 3000 mole phenylethyne/g.at.Pd/hour.

EXAMPLE 12

With the same catalyst system as in Examples 9 and 10, propyne was converted with carbon monoxide and glucose (10 gram) in 50 ml N-methylpyrrolidone in one hour at 40° C. The selectivity of conversion of propyne into the glucose ester of methacrylic acid was 95% and the mean conversion rate was 1300 mole propyne/g.at.Pd/hour.

EXAMPLE 13

With the same catalyst system as in Examples 9, 10 and 12, propyne was converted with carbon monoxide, water (10 ml) and N-methylpyrrolidone (40 ml) in one hour at 50° C. The selectivity of conversion into methacrylic acid was 98% and the mean conversion rate was 20,000 mole propyne/g.at.Pd/hour.

EXAMPLE 14

The same catalyst system as used in Examples 9, 10, 12 and 13 was used in an experiment for converting propyne with carbon monoxide and di-acetone-d-glucose (10 gram) in toluene (80 ml) in one hour at 40° C. The selectivity of the conversion of propyne into di-acetone-d-glucose ester of methacrylic acid was greater than 98% and the mean conversion rate was 1000 mole propyne/g.at.Pd/hour.

What is claimed is:

1. A process for the preparation of an alpha,beta-olefinic unsaturated compound comprising the steps of contacting an acetylenic unsaturated compound with carbon monoxide in the presence of a hydroxyl-containing compound in liquid phase, in the presence of a catalytic system formed from:
   (a) a palladium compound
   (b) a protonic acid, and
   (c) an organic phosphine according to the formula:

wherein $R_1$ is selected from the group consisting of a nitrogen-containing heterocyclic five-atom ring, a nitrogen-containing heterocyclic six-atom ring, a fused ring comprising at least one nitrogen-containing five-atom ring and a fused ring comprising at least one nitrogen-containing six-atom ring; wherein $R_2$ and $R_3$ are each $R_1$ or an aryl group.

2. The process as claimed in claim 1, characterized in that the heterocyclic rings in the definitions of $R_1$, $R_2$ and $R_3$ are individually selected from the group consisting of pyridyl, pyrazinyl, quinolyl, isoquinolyl, pyrimidinyl, pyridazinyl, indolizinyl, cinnolinyl, acridinyl, phenazinyl, phenanthridinyl, phenanthrolinyl, phthalazinyl, naphthyrindinyl, quinoxalinyl and quinazolinyl.

3. The process as claimed in claim 1, characterized in that the heterocyclic groups are selected individually from the group consisting of pyridyl, pyrazinyl and pyridazinyl.

4. The process as claimed in claim 1, characterized in that at least one of $R_2$ and $R_3$ represents a phenyl.

5. The process as claimed in claim 1, characterized in that at least one of said heterocyclic and aryl groups is (are) substituted with at least one electron-repelling group(s).

6. The process as claimed in claim 5, characterized in that the electron-repelling group(s) are selected from the group consisting of alkoxy groups with 1 to 5 carbon atoms, alkyl groups with 1 to 5 carbon atoms, dimethylamino and diethylamino groups.

7. The process as claimed in claim 6, characterized in that the electron-repelling group(s) are selected from the group consisting of p-methoxy, o-methoxy, p-ethoxy, o-ethoxy, methyl, ethyl and dimethylamino groups.

8. The process as claimed in claim 7, characterized in that the electron-repelling group(s) are methyl groups.

9. The process as claimed in claim 6, characterized in that the electron-repelling group(s) are alkyl groups with 1 to 5 carbon atoms.

10. The process as claimed in claim 1, characterized in that at least one of said heterocyclic and aryl groups is (are) substituted with at least one electron-attracting group(s).

11. The process as claimed in claim 8, characterized in that the electron-attracting group(s) are selected from the group consisting of chlorine, fluorine, trifluoromethyl, trichloromethyl, monochloromethyl and m-methoxy groups.

12. The process as claimed in claim 1 wherein $R_1$ represents pyridyl, $R_2$ is pyridyl or phenyl and $R_3$ is phenyl.

13. The process as claimed in claim 1, characterized in that said protonic acid is para-toluic sulfonic acid or benzenephosphoric acid.

14. The process as claimed in claim 1, characterized in that said palladium compound is palladium acetate.

15. The process as claimed in claim 1, characterized in that the quantity of palladium compound used is from about $10^{-7}$ to about $10^{-1}$ gram atom palladium per mole acetylenic unsaturated compound.

16. The process as claimed in claim 1, characterized in that the molar ratio of the organic phosphine to the palladium compound is between about 2 and about 500 mole organic phosphine per gram atom palladium.

17. The process as claimed in claim 1, characterized in that the number of protonic acid equivalents per organic phosphine equivalent is between about 0.1 and about 50.

18. The process as claimed in claim 1, characterized in that N-methylpyrrolidone is used as main solvent or co-solvent.

19. The process as claimed in claim 1, characterized in that the molar quantity of the hydroxyl-containing compound per mole acetylenic unsaturated compound is between about 0.01 and about 100.

20. The process as claimed in claim 1, characterized in that said acetylenic unsaturated compound is selected from the group consisting of acetylene, propyne and phenylacetylene.

21. The process as claimed in claim 1, characterized in that said hydroxyl containing reactant is a lower sugar.

22. The process as claimed in claim 1, characterized in that $R_1$ is a nitrogen-containing heterocyclic ring substituted by one or more alkyl group with 1 to 5 carbon atoms.

23. The process as claimed in claim 22, characterized in that $R_2$ is a nitrogen-containing heterocyclic ring substituted by one or more alkyl groups with 1 to 5 carbon atoms.

24. The process as claimed in claim 23, characterized in that $R_3$ is a nitrogen-containing heterocyclic ring substituted by one or more alkyl groups with 1 to 5 carbon atoms.

25. A process for the preparation of methyl methacrylate by the carbonylation of propyne with carbon monoxide in the presence of methanol using a catalytic system formed from:
(a) from about $10^{-7}$ to about $10^{-1}$ gram atom palladium (II) acetate per mole of propyne;
(b) from about 2 to about 500 mole per gram atom of palladium of a phosphine selected from the group consisting of diphenyl-2-pyridyl phosphine, phenyl-di(2-pyridyl)phosphine, tri(2-pyridyl) phosphine and a mixture thereof; and
(c) from about 0.1 to about 50 equivalent of para-toluene sulfonic acid or benzene phosphoric acid per equivalent of the phosphine.

26. A catalytic system consisting of:
(a) a palladium compound
(b) a protonic acid, and
(c) an organic phosphine according to the formula:

wherein $R_1$ is selected from the group consisting of a nitrogen-containing heterocyclic iive-atom ring, a nitrogen-containing heterocyclic six-atom ring, a fused ring comprising at least one nitrogen-containing five-atom ring and a fused ring comprising at least one nitrogen-containing six-atom ring; wherein $R_2$ and $R_3$ are each $R_1$ or an aryl group.

27. The catalytic system as claimed in claim 26, characterized in that the heterocyclic rings in the definitions of $R_1$, $R_2$ and $R_3$ are individually selected from the group consisting of pyridyl, pyrazinyl, quinolyl, isoquinolyl, pyrimidinyl, pyridazinyl, indolizinyl, cinnolinyl, acridinyl, phenazinyl, phenanthridinyl, phenanthrolinyl, phthalazinyl, naphthyridinyl, quinoxalinyl and quinazolinyl.

28. The catalytic system as claimed in claim 26, characterized in ihat the heterocyclic groups are selected individually from pyridyl, pyrazinyl and pyridazinyl.

29. The catalytic system as claimed in claim 26, characterized in that at least one of $R_2$ and $R_3$ represent a phenyl.

30. The catalytic system as claimed in claim 26, characterized in that $R_1$ represents pyridyl, $R_2$ represents pyridyl or phenyl and $R_3$ represents phenyl.

31. The catalytic system as claimed in claim 26, characterized in that the molar ratio of the phosphine to the palladium compound is between about 2 and about 500 mole phosphine per gram atom palladium.

32. The catalytic system as claimed in claim 26, characterized in that the number of protonic acid equivalents per phosphine equivalent is between about 0.1 and about 50.

33. A catalyst formed from
(a) palladium (II) acetate;
(b) a phosphine selected from the group consisting of diphenyl-2-pyridyl phosphine, di-(2-pyridyl)phosphine, tri(2-pyridyl) phosphine and a mixture thereof; and
(c) para-toluene sulfonic acid or benzene phosphoric acid.

* * * * *

UNITED STATES PATENT AND TRADEMARK OFFICE
CERTIFICATE OF CORRECTION

PATENT NO. : 4,940,787
DATED : July 10, 1990
INVENTOR(S) : Eit Drent

It is certified that error appears in the above-identified patent and that said Letters Patent is hereby corrected as shown below:

Column 10, line 64, at the first line of claim 11, for the claim reference number "8", should read --10--.

Signed and Sealed this

Twenty-third Day of March, 1993

Attest:

STEPHEN G. KUNIN

*Attesting Officer*      *Acting Commissioner of Patents and Trademarks*